(12) United States Patent
Tsujii

(10) Patent No.: US 7,257,190 B2
(45) Date of Patent: Aug. 14, 2007

(54) RADIOGRAPHIC DEVICE AND CONTROL METHOD THEREFOR

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 97 days.

(21) Appl. No.: 10/844,797

(22) Filed: May 13, 2004

(65) Prior Publication Data

US 2004/0228434 A1  Nov. 18, 2004

(30) Foreign Application Priority Data

May 14, 2003 (JP) .............................. 2003-135794

(51) Int. Cl.
*H05G 1/60* (2006.01)
*A61B 6/03* (2006.01)
*A61B 6/04* (2006.01)

(52) U.S. Cl. .............................. 378/62; 378/10; 378/15; 378/16; 378/20; 378/108

(58) Field of Classification Search ..................... 378/4, 378/8, 15, 16, 19, 20, 95, 96, 97, 98.8, 108, 378/115, 116, 197, 10, 62
See application file for complete search history.

(56) References Cited

U.S. PATENT DOCUMENTS

| | | | | |
|---|---|---|---|---|
| 5,355,309 A * | 10/1994 | Eberhard et al. | ............... | 378/15 |
| 5,386,446 A * | 1/1995 | Fujimoto et al. | ............... | 378/20 |
| 6,222,906 B1 * | 4/2001 | Sakaguchi et al. | ......... | 378/98.8 |
| 6,233,308 B1 * | 5/2001 | Hsieh | ........................... | 378/62 |
| 6,298,111 B1 * | 10/2001 | Ozaki | ............................... | 378/8 |
| 6,324,243 B1 * | 11/2001 | Edic et al. | ...................... | 378/4 |
| 6,470,068 B2 * | 10/2002 | Cheng | ........................... | 378/20 |
| 6,504,892 B1 * | 1/2003 | Ning | .............................. | 378/4 |
| 6,504,894 B2 * | 1/2003 | Pan et al. | ......................... | 378/8 |
| 6,707,881 B2 * | 3/2004 | Boehm et al. | .............. | 378/98.7 |
| 6,741,671 B2 * | 5/2004 | Dunham et al. | ................ | 378/4 |
| 6,744,848 B2 * | 6/2004 | Stanton et al. | ................. | 378/55 |

FOREIGN PATENT DOCUMENTS

| | | |
|---|---|---|
| JP | 5-212022 | 8/1993 |
| JP | 6-054838 | 3/1994 |
| JP | 8-299321 | 11/1996 |
| JP | 2001-218767 | 8/2001 |

OTHER PUBLICATIONS

English Abstract for Japanese Patent Laid Open No. 2001-218767.
English Abstract for Japanese Patent Laid Open No. 8-299321.
English Abstract for Japanese Patent Laid Open No. 6-054838.
English Abstract for Japanese Patent Laid Open No. 5-212022.

* cited by examiner

*Primary Examiner*—Allen C. Ho
(74) *Attorney, Agent, or Firm*—Morgan & Finnegan, L.L.P.

(57) ABSTRACT

A radiographic device includes a radiation source which generates radiation and a detector which detects radiation from the radiation source on a two-dimensional plane and outputs an image signal, and performs radiography of a subject to be examined while rotating the radiation source and the detector relative to the subject. In this radiography, the first resolution or the second resolution lower than the first resolution is selected in accordance with a rotational position in the relative rotation. An image signal from the detector is stored as data corresponding to the resolution selected by a selection unit.

16 Claims, 7 Drawing Sheets

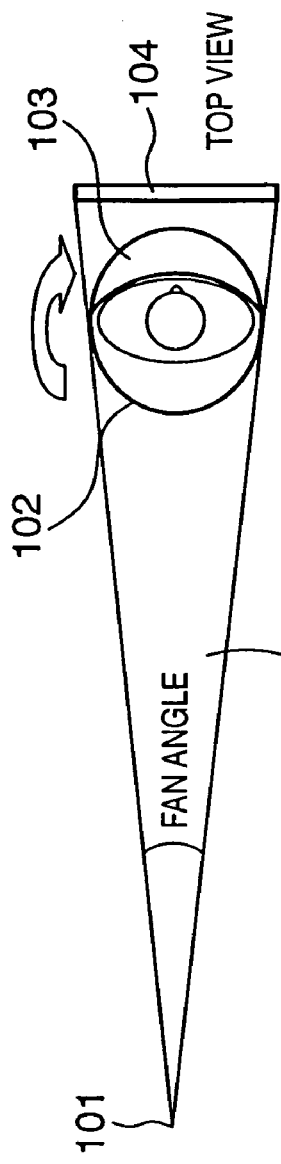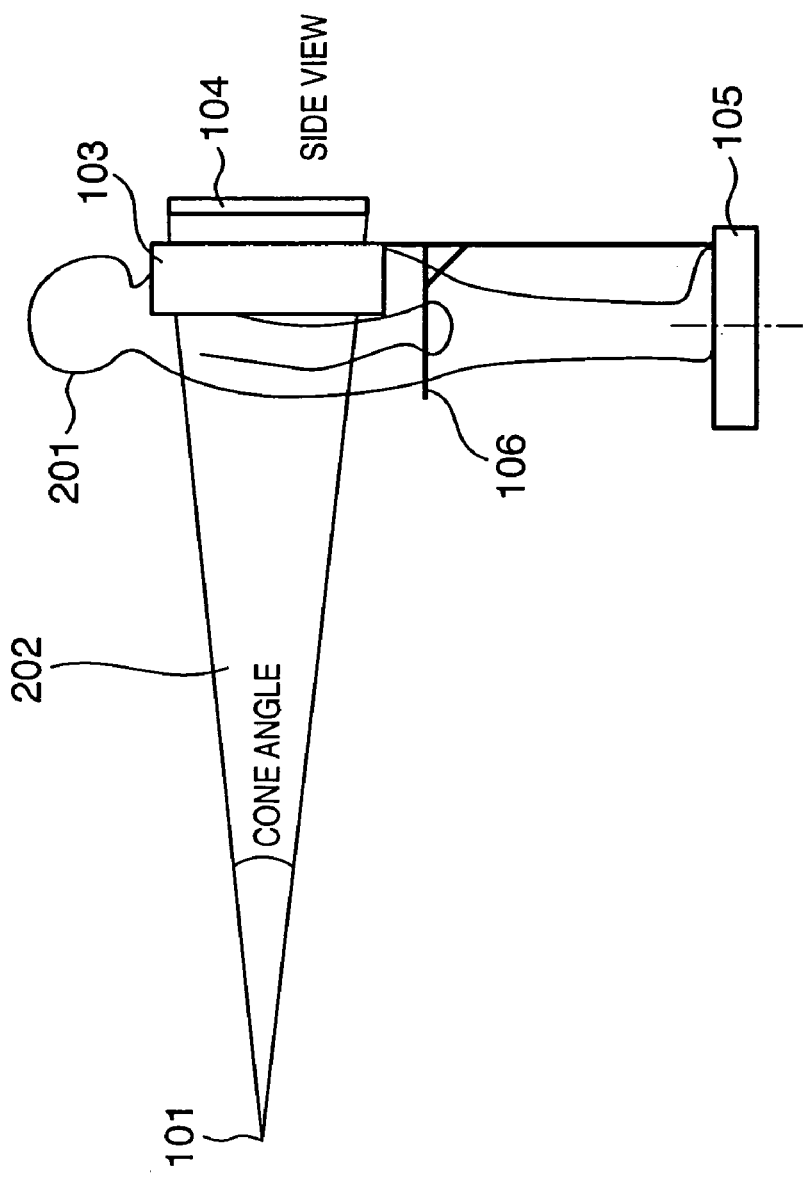
FIG. 1A
FIG. 1B

US 7,257,190 B2

RADIOGRAPHIC DEVICE AND CONTROL METHOD THEREFOR

FIELD OF THE INVENTION

The present invention relates to a radiation imaging technique of imaging a radiation characteristic distribution in a subject to be examined by using radiation in general like an X-ray CT device or the like which performs imaging by using radiation such as X-rays.

BACKGROUND OF THE INVENTION

A conventional X-ray CT device has been known, which irradiates a subject to be examined with X-rays, detects X-rays transmitted through the subject or scattered by the subject with an X-ray detector, and provides a fluoroscopic image, tomogram, or three-dimensional image of the subject on the basis of the X-ray detection output (X-ray photon count).

Such X-ray CT devices are classified into a fan beam type and a cone beam type according to the beam shapes of X-rays. A general X-ray CT device uses a fan beam as an X-ray beam which is thin in the Z direction (a direction perpendicular to a tomographic surface). A cone beam CT device using a cone beam has recently been developed. This device uses an X-ray beam which also spreads in the Z direction. A CT device using a cone beam will be referred to as a cone beam CT device (CBCT device) hereinafter.

As this CBCT, a conventional CT (i.e., having only one row of detection elements) in a form equivalent to a so-called third-generation type or a scheme called an R/R type has recently been studied. The third-generation type (R/R type) CT is designed to perform scanning (acquisition of projection data) while making a pair of an X-ray source and a detector rotate around a subject to be examined.

FIG. 4 is a view showing an example of a CBCT device. The CBCT device shown in FIG. 4 belongs to third-generation type CT devices, and makes both an X-ray source (X-ray tube 401) and an X-ray detector 402 pivot around a subject to be examined. They make one rotation to complete scanning a region of interest.

In a general X-ray CT device, detection elements are arranged in one line in a channel (CH) direction to sample in this direction. Each element is identified by a channel number. In contrast to this, in a CBCT device, as shown in FIG. 4, detection elements are also arranged in the Z direction (row direction). That is, the detector of the CBCT device has detection elements two-dimensionally arranged in the form of an orthogonal lattice.

According to such a CBCT device, detection elements are arranged in the two directions, i.e., the Z direction (row direction) and CH direction, in the form of a lattice to form a detector, and radiation is applied in the form of a cone by making it have a thickness in the Z direction as well, thereby obtaining projection data corresponding to a plurality of columns at once.

X-ray imaging diagnosis generally uses both some radiography and X-ray CT. Radiography is used for initial diagnosis, whereas CT is used for detailed diagnosis. It, however, does not mean that CT images make radiography unnecessary because general radiography makes it possible to comprehensively grasp the condition of a patient.

A positioning image (called a scanogram, scout image, or the like) is sometimes taken by using a CT sensor before CT imaging. This image can be regarded as a projection image such as an image obtained by radiography. A scanogram is described in, for example, Japanese Patent Laid-Open No. 2001-218767. In general, a CT sensor is about 1 mm square, and hence lacks in resolution. The resolution of a scanogram is therefore not enough to be used for diagnosis based on radiography. In order to obtain both a CT image and a radiography, an X-ray CT device and X-ray imaging device need to be separately prepared. That is, a plurality of devices (facilities) must be purchased.

The present invention has been made in consideration of the above problems, and is configured to acquire radiographys during acquisition of CBCT data in a CBCT device using an FPD (Flat Panel Detector) in consideration of the fact that when the FPD is sufficiently large in size, CT projection data itself has an area corresponding to radiography. In this case, problems are posed in terms of resolution and radiation dose. In general, CT data are acquired at high speed (1,000 frames per sec), but low in resolution. In addition, the S/N ratio of such data is lower than that of data obtained by radiography. This may make it necessary to change the imaging form during CT scanning.

As will be described below, arrangements designed to change the imaging form during scanning are described in Japanese Patent Laid-Open Nos. 08-299321, 05-212022, and 06-054838. None of these arrangements is aimed at obtaining a radiography for diagnosis during CT scanning, and there is no indication of an arrangement which can realize it.

Japanese Patent Laid-Open No. 08-299321 has an object to solve the following problem. When imaging is to be continuously done by helically scanning the first and second imaging regions while the rotational speeds (scan speeds) of an X-ray source and detector are changed, the positional information of a top (table on which a subject to be examined is placed) which is calculated by a data acquisition electronics (DAS) after the start of change in rotational speed deviates from the actual positional information of the top. This makes it impossible to accurately obtain a tomogram of a desired region.

According to Japanese Patent Laid-Open No. 08-299321, the rotational speeds of the X-ray and X-ray detector can be changed, and the translational speed of the top is controlled in accordance with the rotational speeds of the X-ray and X-ray detector. When at least the rotational speeds of the X-ray and X-ray detector change, the current rotational speeds of the X-ray and X-ray detector are obtained on the basis of the positional information of the X-ray and X-ray detector which is detected by a rotational position detection means, and the translational speed of the top is controlled on the basis of this positional information.

As described above, Japanese Patent Laid-Open No. 08-299321 discloses an arrangement which acquires data while changing the scan speed of the CT device. However, this arrangement is not designed to obtain a radiography for diagnosis during CT scanning, and there is no description about of it.

Japanese Patent Laid-Open No. 05-212022, describes a data recording method wherein the scan/rotational speed or bed speed is changed. In an embodiment, there is the description "Scanning is continuously completed by changing imaging conditions in accordance with the region to be imaged. For example, for a chest portion, the movement amount of the bed is set to be relatively small to increase the resolution, whereas for an abdominal portion, the movement amount of the bed is set to be relatively large." This technique is aimed at increasing the slice resolution in the body axis direction by adjusting the movement amount of the bed, but does not imply a change in data resolution when the sensor itself, which performs data acquisition, is taken into consideration. That is, with the technique disclosed in Japanese Patent Laid-Open No. 05-212022, a radiography for diagnosis cannot be obtained either during CT scanning, and there is no description of it.

Japanese Patent Laid-Open No. 06-054838 discloses a CT device in which when different speed ranges are input and set depending on the region to be screened and the region to be closely examined, command signals corresponding to the settings are supplied from the rotational speed commanding device of a motor to a servo amplifier. The servo amplifier then rotates/drives the motor in accordance with the above settings to cause a bed driving mechanism to move the bed at different moving speeds for the region to be screened and the region to be closely examined. A bed position detector feeds back the position data of the subject on the bed to the rotational speed commanding device of the motor to make a correction such that command signals are supplied from the rotational speed commanding device of the motor to the servo amplifier in accordance with the settings made by a speed setting device.

For example, switching control of the moving speed of the bed is performed to scan the cerebral basal region with a slice width of about 1 or 2 mm, and the cerebral region with a slice width of about 5 or 10 mm, thereby shortening the imaging time without degrading the image quality of an image of the cerebral basal region. This reference also discloses a technique of performing switching control of the rotational speed of the X-ray (gantry) in the data acquisition unit, i.e., the changing speed in the projection direction instead of shortening the imaging time and controlling artifacts by switching control of the moving speed of the bed.

According to Japanese Patent Laid-Open No. 06-054838, the resolution of slice data for reconstruction is changed depending on the region to be imaged on the basis of the relationship between the table speed and the scan speed. Obviously, however, this reference discloses no technical idea of obtaining a radiography for diagnosis during CT scanning.

SUMMARY OF THE INVENTION

The present invention has been made in consideration of the above problems, and has as its object to acquire a radiography which can be used for diagnosis during CT imaging operation.

In order to achieve the above object, a radiographic device according to the present invention has the following arrangement. That is, a radiographic device according to one aspect of the present invention comprises: a radiation source which generates radiation; a detector which detects radiation from the radiation source on a two-dimensional plane and outputs an image signal; an imaging control unit configured to perform radiography of a subject to be examined while rotating the radiation source and the detector relative to the subject; a selection unit configured to select one of a first resolution and a second resolution lower than the first resolution in the radiography in accordance with a rotational position in the relative rotation; and a storage unit configured to store data corresponding to a resolution selected by the selection unit on the basis of the image signal from the detector.

In addition, according to another aspect of the present invention, in order to achieve the above object, there is provided a control method for a radiographic device including a radiation source which generates radiation and a detector which detects radiation from the radiation source on a two-dimensional plane and outputs an image signal, comprising: an imaging control step of performing radiography of a subject to be examined while rotating the radiation source and the detector relative to the subject; a selection step of selecting one of a first resolution and a second resolution lower than the first resolution in the radiography in accordance with a rotational position in the relative rotation; and a storage step of storing data corresponding to a resolution selected in the selection step on the basis of the image signal from the detector.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 1A and 1B are views showing the schematic arrangement of an X-ray CT device according to the first embodiment;

DETAILED DESCRIPTION OF THE PREFERRED EMBODIMENTS

Figure 2A:
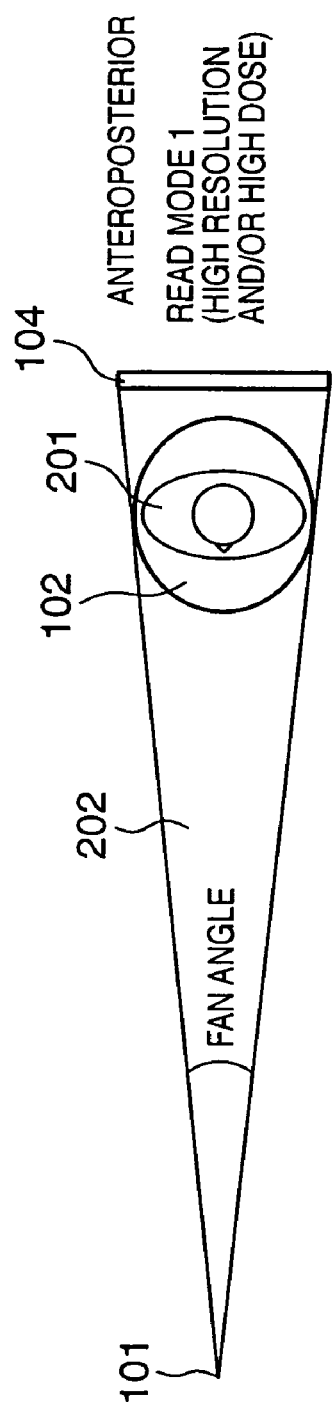
FIGS. 2A, 2B, and 2C are conceptual views showing CT imaging operation in the first embodiment.

Preferred embodiments of the present invention will now be described in detail in accordance with the accompanying drawings.

First Embodiment

FIGS. 1A and 1B are views showing the schematic arrangement of an X-ray CT device according to the first embodiment. X-rays 202 in the form of a cone beam emitted from an X-ray focus 101 reach a two-dimensional detector 104 upon being attenuated by a subject 201 to be examined. The subject 201 is placed on a subject rotating unit 105 and rotated during scanning. The subject 201 presses his/her breast against a breast pad portion 103 fixed to the subject rotating unit 105 and holds a fixing bar 106. This prevents from the body of the subject 201 from moving during rotation.

A reconstruction area 102 is determined by the X-ray focus 101, two-dimensional detector 104, and subject rotating unit 105. If, for example, the distance from the X-ray focus 101 to the reconstruction center is 200 cm, and the two-dimensional detector 104 has a size of 43 (H)×45 (W)

cm, a reconstruction area having a diameter of 40 cm can be ensured, which is most suitable for CT imaging of a chest portion. Note that the resolution of the two-dimensional detector 104 is 250×250 μm.

Figure 2B:
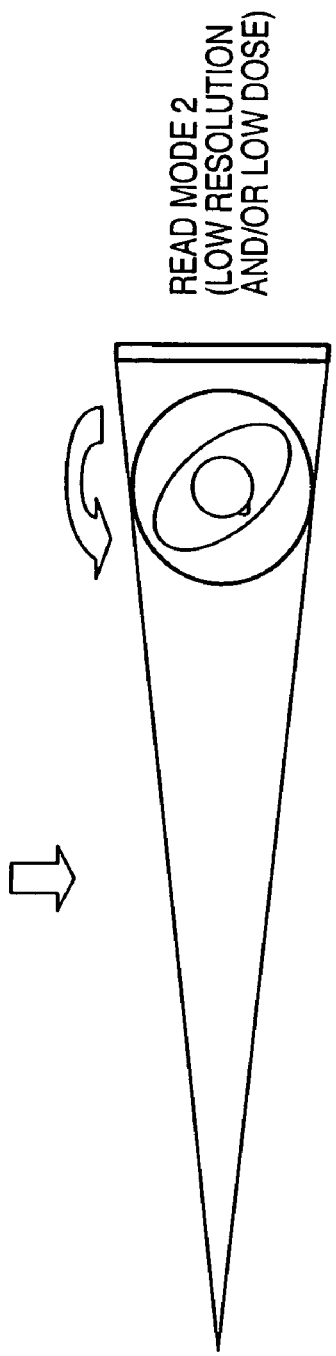
Figure 2C:
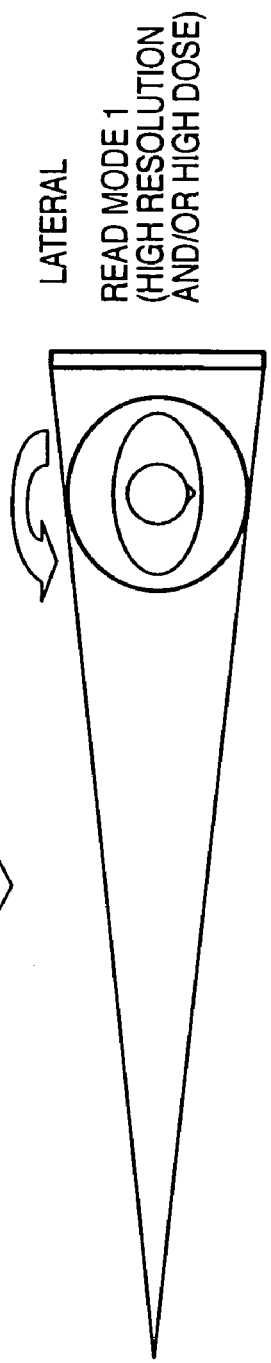

FIGS. 2A to 2C are conceptual views showing CT imaging operation in the first embodiment. FIGS. 2A to 2C sequentially show the progression of scanning in CT imaging. FIGS. 2A to 2C show how the subject 201 is rotated counterclockwise from the anteroposterior imaging position. Note that the scan rotation angle depends on whether CT imaging is performed in the full scan mode or half scan mode. CT imaging may be performed in either of the modes.

Assume that in this case, the half scan mode is used, and the data of an anteroposterior image is acquired in read mode 1 at the start of scanning (FIG. 2A). Read mode 1 is a mode of capturing data with a full resolution of 250×250 μm. In this mode, the data transfer time is about 20 msec. At positions except that anteroposterior position, data acquisition is performed in read mode 2 (FIG. 2B). In read mode 2, analog addition of 2×2 pixels is performed in the two-dimensional detector 104. The addition signal is A/D-converted. Therefore, the read time is about ¼ that in read mode 1, i.e., about 5 msec. When the subject is further rotated to be set at a lateral position, data acquisition is performed in read mode 1 again (FIG. 2C). Thereafter, data acquisition is continued in read mode 2 until the completion of half scanning.

With the above operation, precise image data can be acquired from the anteroposterior and lateral portions of the subject to which read mode 1 is applied. In the above case, half scanning is performed, and so scanning is performed only once at the anteroposterior and lateral positions each. In the case of full scanning, there are two rotational positions for anteroposterior images, i.e., a position for AP (a technique of performing imaging by applying X-rays from the breast side with a sensor being placed on the back side) and a position for PA (a technique of performing imaging by applying X-rays from the back side with a sensor being placed on the breast side), and two rotational positions for lateral images, i.e., a position for LR (a technique of performing imaging by applying X-rays from the left side of the chest with a sensor being placed on the right side) and a position for RL (a technique of performing imaging by applying X-rays from the right side of the chest with a sensor being placed on the left side). In performing imaging for anteroposterior and lateral images each, data acquisition may be performed in high-resolution read mode 1 at both positions (AP and PA or LR and RL). In general, however, imaging is performed in read mode 1 at one of the anteroposterior positions and one of the lateral positions, e.g., the PA anteroposterior position and LR lateral position.

Figure 3:
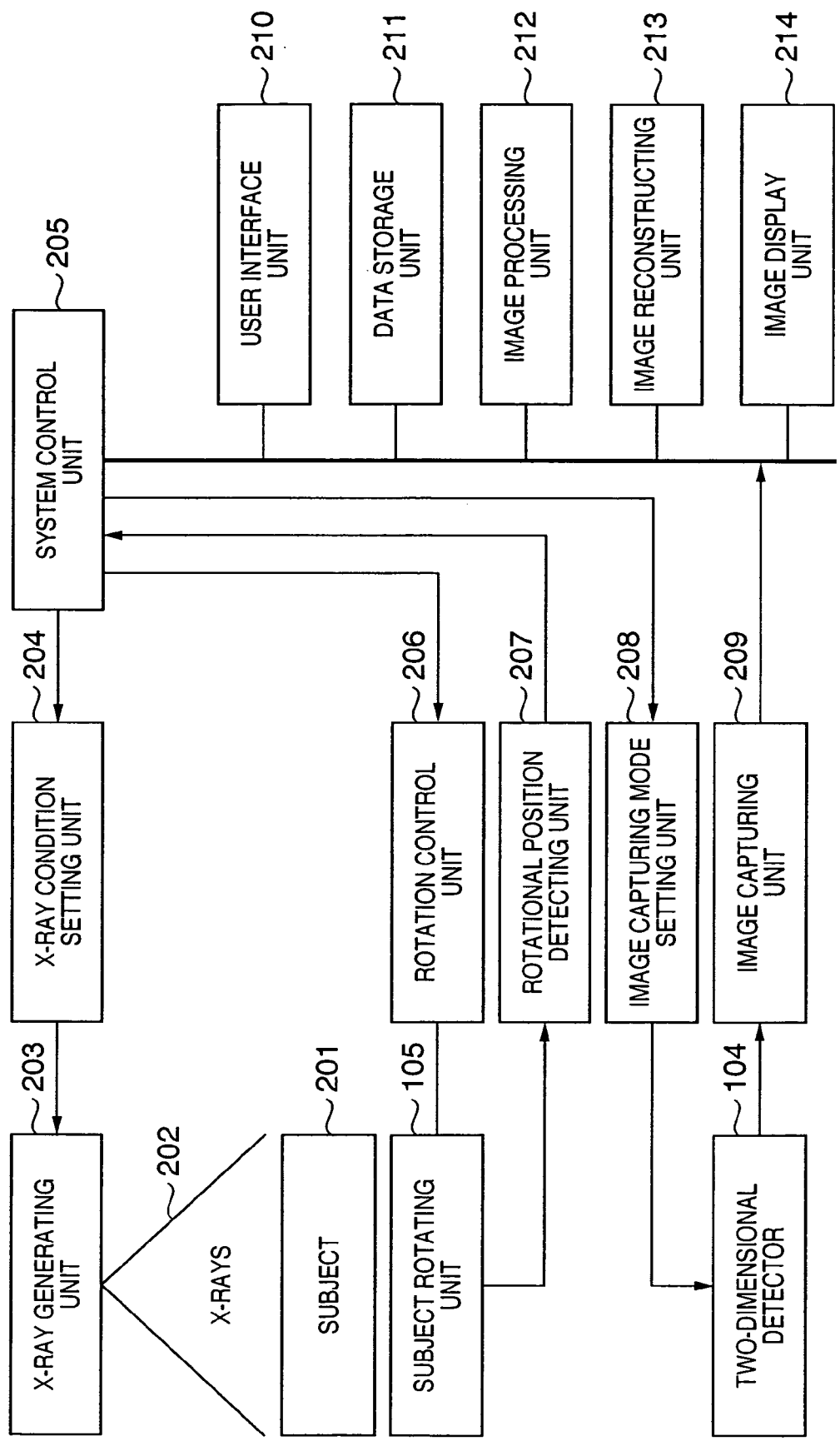
FIG. 3 is a block diagram showing the system mechanism of the X-ray CT device according to the first embodiment.
Figure 4:
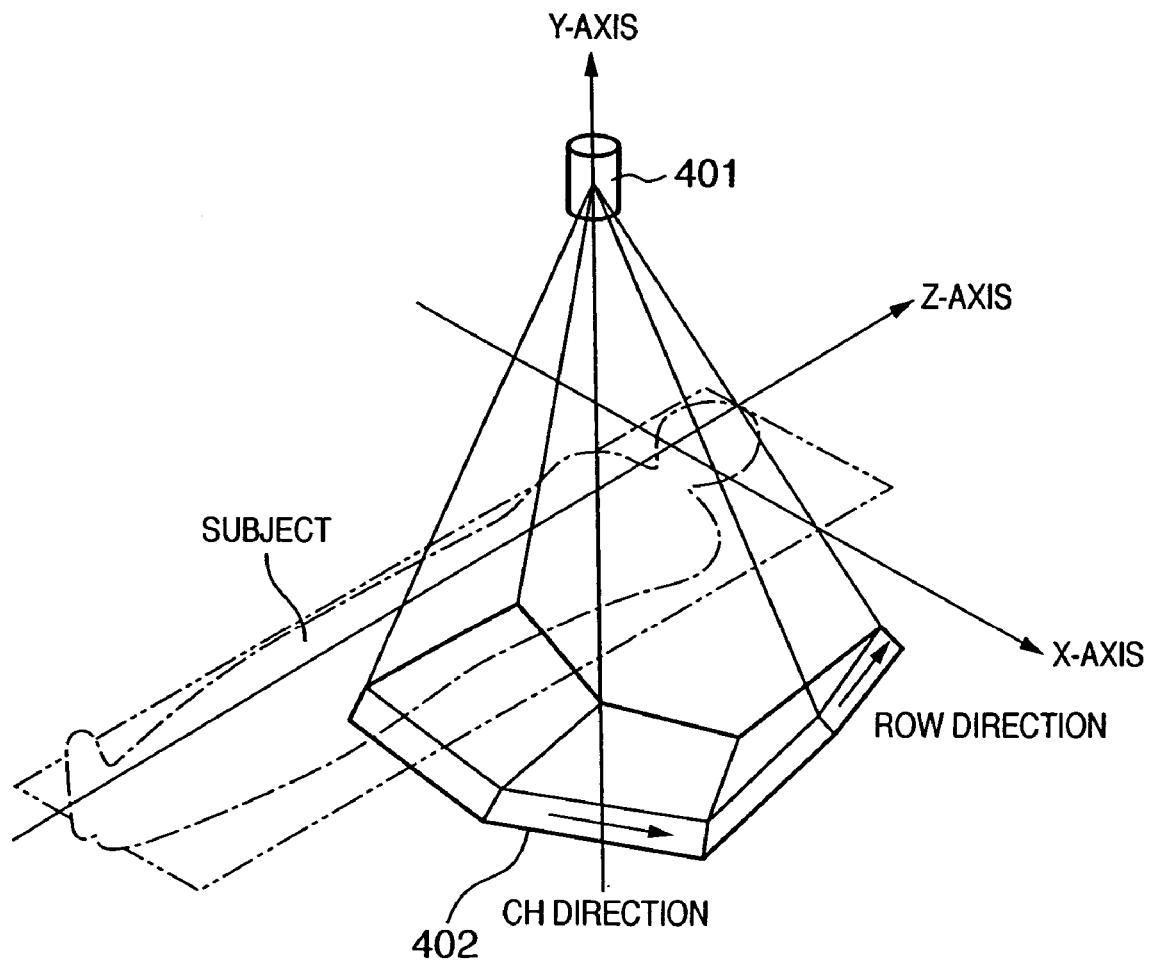
FIG. 4 is a view showing an example of a general CBCT device.

FIG. 3 is a block diagram showing the system mechanism of the X-ray CT device according to the first embodiment. The X-rays 202 emitted from an X-ray generating unit 203 are transmitted through the subject 201 and reach the two-dimensional detector 104. During scanning, the subject 201 is rotated by the subject rotating unit 105. The rotation of the subject rotating unit 105 is controlled by a rotation control unit 206. A rotational position signal is transmitted from the subject rotating unit 105, and the current rotational position of the subject rotating unit 105, i.e., the subject 201, is detected by a rotational position detecting unit 207. In this embodiment, the rotation control unit 206 forms a servo system on the basis of a rotational position signal from the rotational position detecting unit 207.

A system control unit 205 selects a read mode for the two-dimensional detector 104 and X-ray conditions on the basis of a signal from the rotational position detecting unit 207. Anteroposterior and lateral imaging positions are set in the system control unit 205 in advance. At the set rotational positions, data are read in read mode 1. At other positions, data are captured in read mode 2.

As described above, read mode 1 requires an acquisition time four times longer than that required by read mode 2. If, therefore, the scan rotational speed in read mode 1 is set to ¼ that in read mode 2, image blurring due to the rotation of the subject 201 in read mode 1 can be matched with that in read mode 2. This makes it possible to reduce the occurrence of artifacts when an image reconstructing unit 213 reconstructs an image by using both data acquired in read mode 1 and read mode 2. In this manner, the rotation control unit 206 is controlled to change the rotational speed of the subject rotating unit 105 at the anteroposterior and lateral imaging positions stored in the system control unit 205.

Read modes are set by the system control unit 205 through an image capturing mode setting unit 208. The system control unit 205 also sets X-ray conditions. In general, as a radiography, an image having an S/N ratio higher than that of CT data obtained by one exposure, and a higher radiation dose is required because of a high resolution of pixels. At anteroposterior and lateral imaging positions, therefore, tube current control is performed in the X-ray generating unit 203. Note that pulse width control may be performed instead of tube current control. X-ray conditions are set by the system control unit 205 through an X-ray condition setting unit 204.

The data captured from the two-dimensional detector 104 through an image capturing unit 209 is stored in a data storage unit 211. The data stored in the data storage unit 211 is subjected to preprocessing such as offset correction and gain correction in an image processing unit 212. When a CT image is to be reconstructed, the data is also transferred to the image reconstructing unit 213. The image taken in read mode 1 is also used as a radiography. When the data is used for radiography, it is subjected to sharpening processing, grayscale conversion processing, and the like in the image processing unit 212, and the resultant data is output to an image display unit 214.

Careful consideration must be given to gain correction in read mode 1 and read mode 2 before the execution of inverse projection by the image reconstructing unit 213. More specifically, an image in read mode 1 differs in resolution and radiation dose from an image in read mode 2, and hence gain data must be separately measured and prepared. Although imaging in read mode 1 and read mode 2 is performed by using the same sensor, since analog addition is performed in the two-dimensional detector 104 in read mode 2, simple digital addition of high-resolution image data in read mode 1 cannot accurately obtain a gain image in read mode 2. In the case of offset correction as well, offset data acquired in read mode 1 and read mode 2 are used. Because the offset value varies depending on the read mode and integration time to be set.

The difference between the X-ray incident dose in read mode 1 and that in read mode 2 and variations in X-ray incident dose within the same read mode are corrected by a reference detector (not shown). The reference detector is placed near the X-ray tube so as not to count scattered radiation from the patient. The X-rays incident on the reference detector are measured (integrated) at the same timing as the acquisition timing (integration timing) of the two-dimensional detector 104. In general, X-rays vary, and X-rays are applied at different X-ray doses intentionally in still imaging and CT imaging.

Assume that the X-ray incident dose varies. In this case, when the integral amount of the reference detector increases by 5% in linear terms, X-rays which increase in amount by 5% reach the two-dimensional detector 104 even with the same subject. In linear terms, this variation of 5% can be canceled by division. This applies to changes between the read modes. This will be described in detail below.

Let R01 be the reference detector value obtained when gain data is obtained by imaging in read mode 1, and V01 be the detection value of a specific pixel of the two-dimensional detector 104. Likewise, let R02 be the reference detector value obtained when gain data is obtained by imaging in read mode 2, and V02 be the detection Value of the pixel of the two-dimensional detector 104. Then, a constant C which satisfies the following equation can be obtained:

$$V01/R01 = C(V02/R02) \quad (1)$$

where V01 is the average value of four pixels, which corresponds to V02.

Let R11 be the reference detector value obtained when the subject is imaged in read mode 1, and V11 be the detection value of a specific pixel of the two-dimensional detector 104. In this case, in order to generate data X in terms of read mode 2, the following may be calculated:

$$X = (V11/R11)/C \quad (2)$$

In this case, if the constant C is linear with respect all the pixels of the two-dimensional detector 104, the constant C remains almost the same with respect to all the pixels.

As an algorithm for reconstruction, the Feldkamp method "Practical cone-beam algorithm" L. A. Feldkamp, L. C. Davis, and J. W. Kress J. Opt. Soc. Am./Vol. 1, No. 6, pp. 612-619/June 1984 can be used. However, the present invention is not limited to this because many other kinds of reconstruction methods have been proposed. The image reconstructed by the reconstruction unit 213 is displayed on the image display unit 214.

A series of operations from emission of the X-rays 202 to display of a radiography and reconstructed image have been described above with reference to the view showing the system mechanism of the first embodiment. These operations are commanded by a user interface unit 210, and controlled as a whole by the system control unit 205. More specifically, commands from the user interface unit 210 are associated with selection of half scanning or full scanning, X-ray conditions for radiography (if they differ from X-ray conditions for CT imaging), a position for radiography in the full scan mode (PA or AP if a anteroposterior position is to be selected), and the like.

Figure 5:
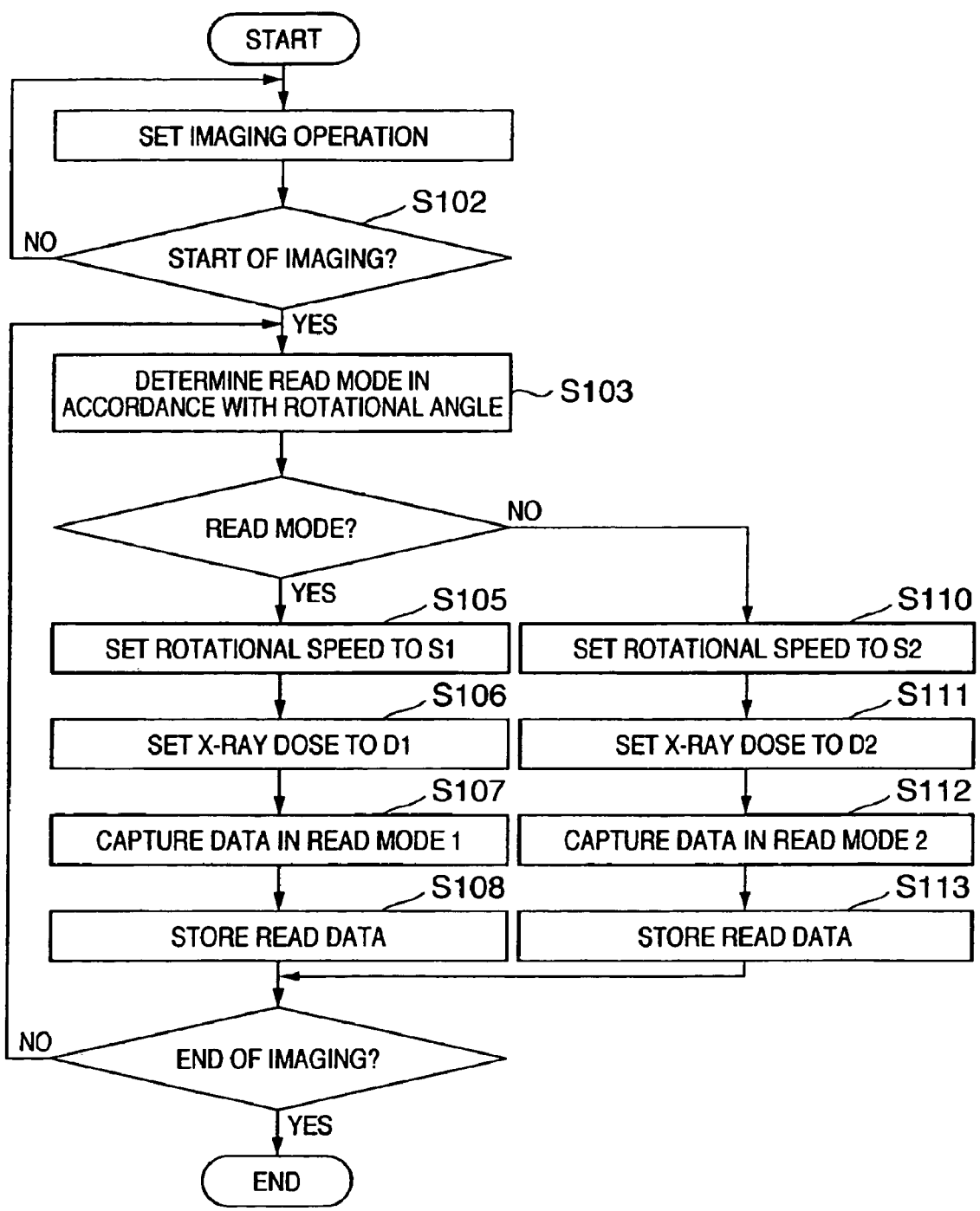
FIG. 5 is a flow chart for explaining processing in X-ray imaging by a CT imaging device according to this embodiment.
Figure 6:
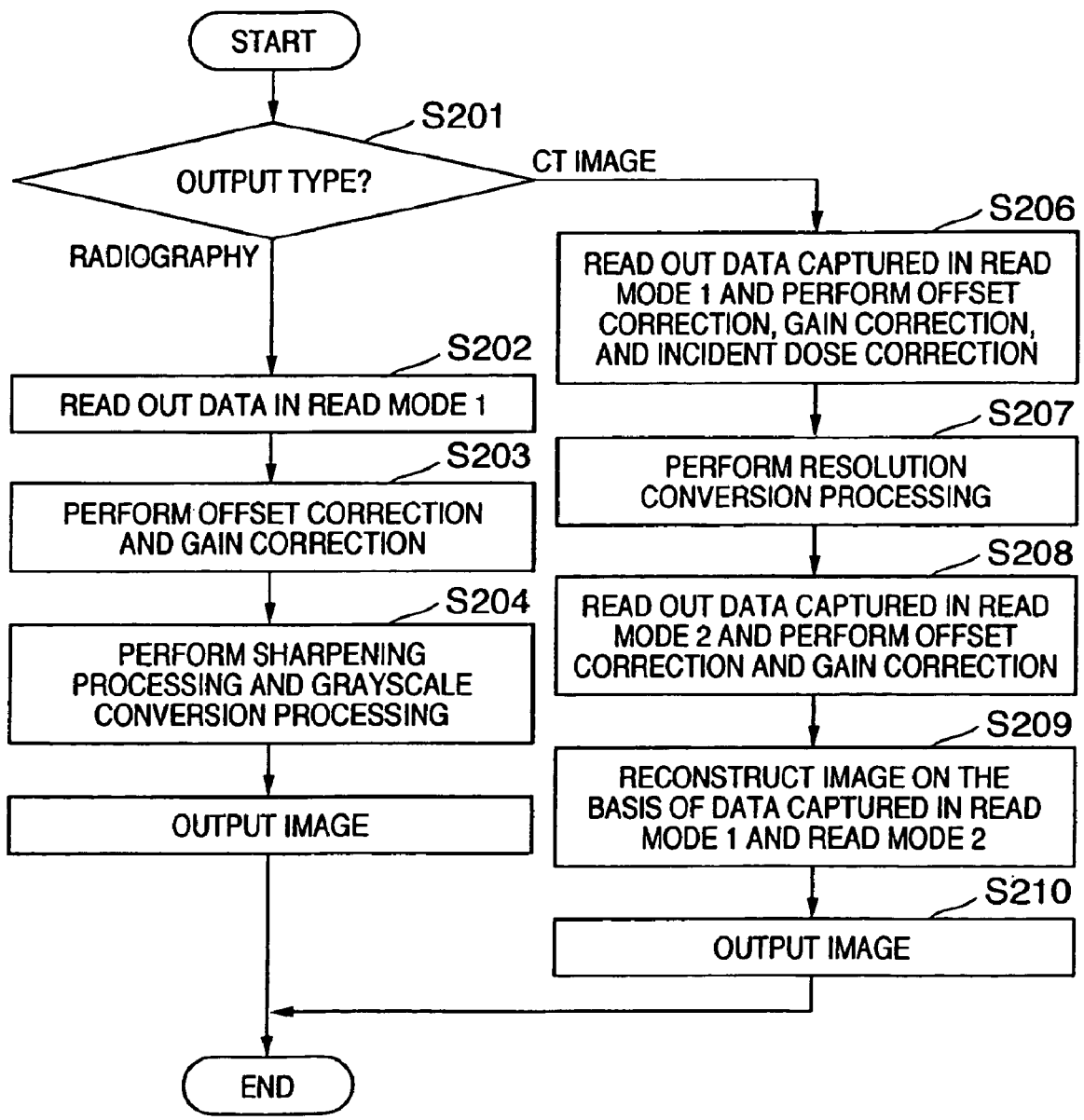
FIG. 6 is a flow chart for explaining output processing of an image taken by the CT imaging device according to this embodiment.
Figure 7:
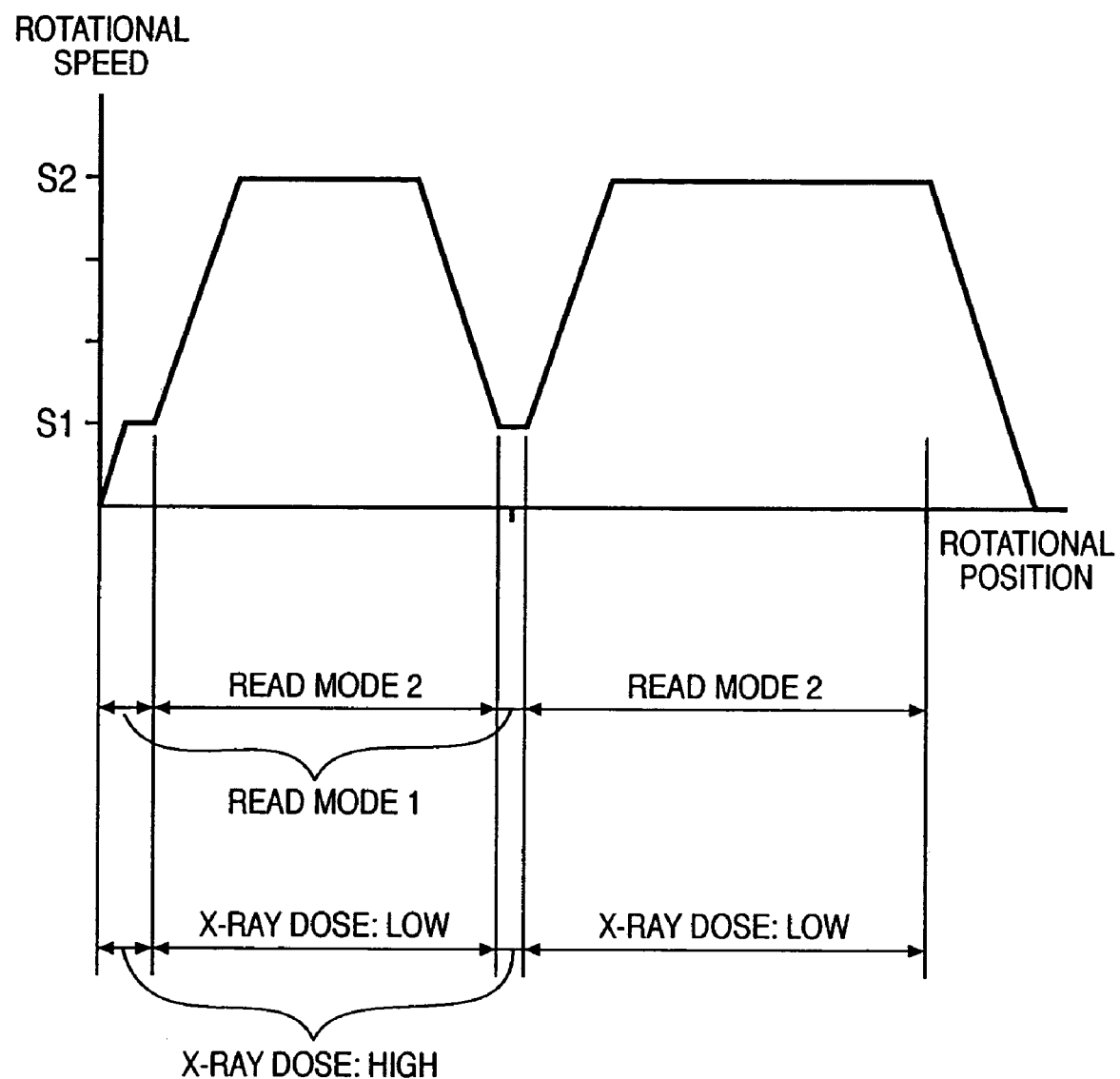
FIG. 7 is a timing chart showing operation in X-ray imaging by the CT imaging device according to this embodiment.

The above operation will be further described below with reference to FIGS. 5 to 7. FIG. 5 is a flow chart for explaining processing in X-ray imaging by the CT imaging device according to this embodiment. FIG. 6 is a flow chart for explaining output processing of an image obtained by imaging by the CT imaging device according to this embodiment. The processing shown in these flow chart is executed by the system control unit 205. FIG. 7 is a timing chart showing the operation in X-ray imaging by the CT imaging device according to this embodiment.

CT imaging operation is set through the user interface unit 210. As described above, the contents to be set include selection of half scanning or full scanning, X-ray conditions for radiography, a position in radiography in the full scan mode (i.e., designation of a range in read mode 1 (e.g., 0° to 10° (anteroposterior position), 85° to 95° (lateral position)), and the like. Note that it is possible to configure the apparatus to set any desired position in radiography in the full scan mode or the half scan mode.

When X-ray imaging is started by the user interface unit 210, the flow advances from step S102 to step S103, and X-ray imaging is executed in both read mode 1 and read mode 2 in accordance with the set contents.

In step S103, a read mode at the current position is determined in accordance with the rotational position obtained by the rotational position detecting unit 207 and the designated range in read mode 1. If read mode 1 is determined in this case, the rotational speed is set to S1 suitable for read mode 1, and the X-ray dose is set to D1 (steps S105 and S106). In step S107, data is read out by the two-dimensional detector 104 in read mode 1. The obtained data is stored in the data storage unit 211 (step S108).

If read mode 2 is determined in step S103, the rotational speed is set to S2 suitable for read mode 2, and the X-ray dose is set to D2 (steps S110 and S111). In step S112, data is read out by the two-dimensional detector 104 in read mode 2. The obtained data is stored in the data storage unit 211 (step S113). Note that when data is to be stored in the data storage unit 211, the data is stored so as to be identifiable as data read out in read mode 1 or read mode 2.

FIG. 7 shows how imaging control is performed in accordance with the above processing. Referring to FIG. 7, at a position corresponding to the rotational speed S1, data for radiography is acquired in read mode 1. Note that since the rotational speed set in each read mode corresponds to the read time for data from the two-dimensional detector 104 as described above, S1<S2. "High" for X-ray dose corresponds to the X-ray dose D1 in FIG. 5; and "low", the X-ray dose D2 in FIG. 5. In general, the dose in read mode which is a high-resolution mode is higher than that in read mode 2 (D1>D2). The above description is based on the assumption that pulse X-rays are used. However, continuous X-rays can also be used. As a modification of the first embodiment which uses continuous X-rays, an X-ray dose may be always kept constant. In this case, since data are acquired depending on angular positions, the integration time of the sensor prolongs with a decrease in rotational speed. An increase in integration time means that the X-ray dose increases with a decrease in speed when constant X-rays are continuously emitted. That is, when imaging is to be done by continuous X-rays, the dose for imaging can be increased by decreasing the speed at a still imaging angle without controlling the X-ray imaging device.

Processing to be performed when an image is to be reconstructed by using the imaging data stored in the data storage unit 211 in the above manner will be described next. When the type of output (radiography or CT image) is designated through the user interface unit 210, the designated type of output is determined in step S201 in FIG. 6.

If the designated output is a radiography, the flow advances to step S202 to read out data in read mode 1 from the data storage unit 211. In step S203, offset correction and gain correction are performed with respect to the data read out in step S202. In step S204, sharpening processing and grayscale conversion processing are performed, and the resultant data is output to the image display unit 214. Note that the image output form is not limited to any display output such as a CRT, and an image may be formed on a film.

If CT image output is designated, the flow advances to step S206 to read out data in read mode 1 from the data storage unit 211 first. Correction about an offset, gain, and incident dose is performed with respect to the read data. As described above, correction about an offset and gain is performed by using offset data and gain correction data acquired in read mode 1. Correction about an incident dose is performed by using a value from the reference detector as described with reference to equations (1) and (2). An X-ray dose in each read mode must be detected by using the reference detector (not shown), and the detection value must be stored in advance. In step S207, resolution conversion processing is performed to match the resolution with that in read mode 2. In step S208, the data acquired in read mode 2 is read out from the data storage unit 211, and offset correction and gain correction performed with respect to the data.

In step S209, a CT image is obtained by performing image reconstruction using the data obtained in step S207 and the data obtained in step S208. In step S210, the reconstructed CT image is output. Note that the image output form is not limited to display output such as a CRT, and an image may be formed on a film.

Second Embodiment

In the first embodiment, different read modes are set at radiography positions and other positions. However, the resolution of reading from a two-dimensional detector 104 need not always be changed. If signals can be read out from the two-dimensional detector 104 at a high resolution of 250×250 μm, the pixel values of 2×2 pixels may be added and averaged outside the detector for CT data. In this case, signals (data) are read out from the two-dimensional detector 104 at a high resolution at two positions, i.e., a position in read mode 1 and a position in read mode 2 which are described in the first embodiment. With regard to data at radiography positions for anteroposterior and lateral portions, the data read out from the two-dimensional detector 104 are stored in a data storage unit 211 without any change. Data at rotational angles which are used only as data for a CT image are added and averaged, and the resultant data is stored in the data storage unit 211. In the second embodiment, there is no need to switch the rotational speed of a subject rotating unit 105.

The operation of the second embodiment will be described with reference to FIG. 5. Steps S105, S106, S110, and S111 can be omitted, and data are captured from the two-dimensional detector 104 in steps S107 and S112 in the same manner (at a high resolution). In read mode 1, captured data are stored in the data storage unit 211 without any change (step S108). In read mode 2, captured data are added/averaged in the above manner, and the resultant data is stored in the data storage unit 211 (step S113).

Note that the above addition/averaging is preferably performed inside an image capturing unit 209, and the resultant data is preferably transferred to the data storage unit 211. This is promising that when the system is formed by using a computer, the load on the system bus can be reduced. In addition, in this embodiment, only high-resolution gain data may be stored. Because the gain data for CT can be obtained by calculation using addition and averaging.

In the second embodiment, only X-ray conditions may be made different from each other in the respective modes. That is, X-ray dose setting in steps S106 and S111 may be executed. In this case, gain correction can be normalized by using a reference detector (not shown) as well as the method described in the first embodiment.

In each of the embodiments described above, a subject is rotated relative to the X-ray generating unit 203 and two-dimensional detector 104. However, the X-ray generating unit 203 and two-dimensional detector 104 may be rotated relative to the subject.

As has been described above, the radiographic device (X-ray CT device) according to each of the above embodiments includes the radiation source (X-ray generating unit 203) which generates radiation and the detector (two-dimensional detector 104) which detects radiation from the radiation source on a two-dimensional plane and outputs an image signal. This device performs imaging of a subject to be examined while rotating the radiation source and detector relative to the subject. In this imaging, the first or second resolution is selected depending on the rotational position in relative rotation (step S103). The device also includes the data storage unit 211 which stores data corresponding to the selected resolution on the basis of an image signal from the detector.

According to the first embodiment, the detector can operate in read mode 1 of outputting an image signal at the first resolution and read mode 2 of outputting an image signal at the second resolution. The data storage unit reads out image signals from the detector upon switching the read modes of the detector in accordance with a rotational position in relative rotation, and stores the read image signals. When the detector is operating in read mode 1, the rotational speed in relative rotation is switched to the low speed.

According to the second embodiment, the detector outputs an image signal at the first resolution, and while the second resolution is selected, the signals obtained from the detector are converted into signals with the second resolution to be stored in the data storage unit at the second resolution.

As described above, in one CT imaging operation, images can be stored at two resolutions, i.e., the first and second resolutions. If, therefore, the first resolution is set to a resolution corresponding to a radiography and the second resolution is set to a resolution corresponding to a CT image, both a radiography and a CT image can be obtained in one CT imaging operation.

According to the above embodiment, since a rotational position where data should be stored at the first resolution can be designated through the user interface unit 210, a radiography can be obtained from a desired position.

In addition, in image reconstruction, a radiography is formed on the basis of data with the first resolution stored in the data storage unit. A CT image is reconstructed by converting data with the first resolution stored in the data storage unit into data with the second resolution and using the resultant data together with data with the second resolution stored in the data storage unit.

As described above, according to each of the above embodiments, a CBCT device using a large two-dimensional detector can obtain both a CT image and a radiography, which have been obtained by imaging by different devices, within single CT imaging operation. That is, the CBCT device can acquire a radiography simultaneously with CT imaging.

As has been described above, according to the present invention, a radiography which can be used for diagnosis can be acquired during CT imaging operation.

As many apparently widely different embodiments of the present invention can be made without departing from the spirit and scope thereof, it is to be understood that the invention is not limited to the specific embodiments thereof except as defined in the appended claims.

What is claimed is:

1. A radiographic device comprising:
   a radiation source which generates radiation;
   a detector which detects radiation from said radiation source on a two-dimensional plane and outputs image data;
   an imaging control unit configured to perform radiography of a subject to be examined while rotating said radiation source and said detector relative to the subject;
   a setting unit which sets a rotational position;
   a selection unit configured to select a first resolution in case of the set rotational position and select a second resolution lower than the first resolution in case of rotational positions except for the set rotational position, in the radiography in the relative rotation;
   a speed control unit configured to switch a speed of the relative rotation to a first speed in case of the set rotational position and switch a speed of the relative rotation to a second speed higher than the first speed in case of rotational positions except for the set rotational positions; and
   a storage unit configured to store image data corresponding to a resolution selected by said selection unit on the basis of the image data from said detector.

2. The device according to claim 1, wherein said detector can operate in a first read mode of outputting the image data at the first resolution and a second read mode of outputting the image data at the second resolution, and said storage unit reads out the image data from said detector upon switching read modes of said detector in accordance with a resolution selected by said selection unit, and stores the read image data.

3. The device according to claim 1, wherein said imaging control unit increases a dose of radiation by said radiation source in case of the set rotational position.

4. The device according to claim 1, further comprising a first construction unit configured to form a radiography on the basis of image data with the first resolution stored in said storage unit.

5. The device according to claim 1, further comprising a second construction unit configured to reconstruct a CT image by using image data obtained by converting image data with the first resolution stored in said storage unit into image data with the second resolution and the image data with the second resolution stored in said storage unit.

6. The device according to claim 5, wherein:
   first correction data acquired under an operation condition set when the image data with the first resolution is acquired and second correction data acquired under an operation condition set when the image data with the second resolution is acquired are held, and
   said second construction unit corrects the image data with the first resolution by using the first correction data, and corrects the image data with the second resolution by using the second correction data.

7. The device according to claim 5, wherein said second construction unit performs incident dose correction with respect to the image data with the first resolution on the basis of a radiation dose for acquiring the image data with the first resolution and a radiation dose for acquiring the image data with the second resolution.

8. The device according to claim 5, further comprising:
   a display unit configured to display a radiography that is formed on the basis of image data with the first resolution stored in said storage unit.

9. A control method for a radiographic device including a radiation source which generates radiation, and a detector which detects radiation from the radiation source on a two-dimensional plane and outputs image data, comprising:
   a setting step of setting a rotational position;
   an imaging control step of performing radiography of a subject to be examined while rotating the radiation source and the detector relative to the subject;
   a selection step of selecting a first resolution in case of the set rotational position and selecting a second resolution lower than the first resolution in case of rotational positions except for the set rotational position, in the radiography in the relative rotation;
   a speed control step of switching a speed of relative rotation to a first speed in case of the set rotational position and switching a speed of the relative rotation to a second speed higher than the first speed in case of a rotational position except for the set rotational position; and
   a storage step of storing image data corresponding to a resolution selected in the selection step on the basis of the image data from the detector.

10. The method according to claim 9, wherein:
    the detector can operate in a first read mode of outputting image data at the first resolution and a second read mode of outputting image data at the second resolution, and
    in the storage step, image data is read out from the detector upon switching read modes of the detector in accordance with a resolution selected in the selection step, and the read image data is stored.

11. The method according to claim 9, wherein in the imaging control step, a dose of radiation generated by said radiation source is increased in case of the set rotational position.

12. The method according to claim 9, further comprising a first construction step of forming a radiography on the basis of image data with the first resolution stored in the storage step.

13. The method according to claim 9, further comprising a second construction step of reconstructing a CT image by using image data obtained by converting image data with the first resolution stored in the storage step into image data with the second resolution and the data with the second resolution stored in the storage step.

14. The method according to claim 13, wherein:
    first correction data acquired under an operation condition set when the image data with the first resolution is acquired and second correction data acquired under an operation condition set when the image data with the second resolution is acquired are held, and
    in the second construction step, the image data with the first resolution is corrected by using the first correction data, and the image data with the second resolution is corrected by using the second correction data.

15. The method according to claim 13, wherein in the second construction step incident dose correction is performed with respect to the image data with the first resolution on the basis of a radiation dose for acquiring the image data with the first resolution and a radiation dose for acquiring the image data with the second resolution.

16. The method according to claim 13, further comprising:
    a display step of displaying a radiography that is formed on the basis of image data with the first resolution stored in said storage step.

* * * * *